United States Patent [19]
Crooks et al.

[11] Patent Number: 5,691,365
[45] Date of Patent: Nov. 25, 1997

[54] NICOTINIC RECEPTOR ANTAGONISTS IN THE TREATMENT OF NEUROPHARMACOLOGICAL DISORDERS

[75] Inventors: Peter A. Crooks; Linda P. Dwoskin, both of Lexington, Ky.; Alain Ravard, Petit-Couronne, France

[73] Assignee: University of Kentucky Research Foundation, Lexington, Ky.

[21] Appl. No.: 503,904

[22] Filed: Jul. 18, 1995

[51] Int. Cl.⁶ ............... A61K 31/44; C07D 401/04
[52] U.S. Cl. ............................ 514/343; 546/279.4
[58] Field of Search ..................... 546/279.4; 514/343

[56] References Cited

U.S. PATENT DOCUMENTS

| | | |
|---|---|---|
| 4,965,074 | 10/1990 | Leeson . |
| 5,069,904 | 12/1991 | Masterson . |
| 5,187,169 | 2/1993 | Lippiello et al. . |
| 5,227,391 | 7/1993 | Caldwell et al. . |
| 5,232,933 | 8/1993 | Lippiello et al. . |
| 5,272,155 | 12/1993 | Americ et al. . |
| 5,276,043 | 1/1994 | Lippiello et al. . |
| 5,278,176 | 1/1994 | Lin . |
| 5,298,257 | 3/1994 | Bannon et al. . |
| 5,316,759 | 5/1994 | Rose et al. . |
| 5,362,496 | 11/1994 | Baker et al. . |
| 5,369,028 | 11/1994 | Harpold et al. . |
| 5,371,188 | 12/1994 | Heinemann et al. . |

OTHER PUBLICATIONS

Huang et al., Journal of the American Society for Mass Spectrometry, vol. 5 (No. 10), pp. 935–948, Elsevier Pub. Oct. 1994.

Chemical Abstracts, vol. 86 (No. 13) abst. No. 90, 110p, Mar. 28, 1977.

Chemical Abstracts, vol. 73 (No. 17) Abst. No. 87,738–a Oct. 26, 1970.

Janson, A.M. et al., "Chronic nicotine treatment decreases dopamine D2 agonist binding in the rat basal ganglia." *Neuroreport,* vol. 3, No. 12, pp. 1117–1120, 1992.

Boksa, P. et al., "Pharmacological activity of N–methyl–carbamylcholine, a novel acetylcholine receptor agonist with selectivity for nicotinic receptors." *Eur. J. Pharmacol.,* vol. 173, No. 1, pp. 93–108, 1989.

Limberger, N. et al., "A search for receptors modulating the release of gamma–[3H]aminobutyric acid in rabbit caudate nucleus slices." *J. Neurochem.,* vol. 46, No. 4, pp. 1109–1117, 1986.

Corcoran, J.J. et al., "Inhibition of calcium uptake, sodium uptake, and catecholamine secretion by methoxyverapamil (D600) in primary cultures of adrenal medulla cells." *J. Neurochem.,* vol. 40, No. 4, pp. 1106–1109, 1983.

Neubig, R.R. et al., "Permeability control by cholinergic receptors in Torpedo postsynaptic membranes: agonist dose–response relations measured at second and millisecond times." *Biochemistry,* vol. 19, No. 12, pp. 2770–2779, 1980.

Clarke, P.B., "Nicotine dependence—mechanisms and therapeutic strategies." *Biochem. Soc. Symp.,* vol. 59, pp. 83–95, 1993.

Abood, L.G. et al., "Sites, mechanisms, and structural characteristics of the brain's nicotine receptor." *J. Subst. Abuse,* vol. 1, No. 3, pp. 259–271, 1989.

Calogero, A.E. et al., "Effect of cholinergic agonists and antagonists on rat hypothalamic corticotropin–releasing hormone secretion in vitro." *Neuroendocrinology,* vol. 47, No. 4, pp. 303–308, 1988.

*Primary Examiner*—Alan L. Rotman
*Attorney, Agent, or Firm*—Lowe, Price, LeBlanc & Becker

[57] ABSTRACT

Nicotine analogs that have nicotinic receptor antagonist properties. These compounds have been shown to competitively inhibit dopamine release induced by nicotine. The nicotine analog compounds are useful in the treatment of nicotine abuse, smoking cessation therapy, as an antidote for nicotine intoxication, treatment of cognitive disorders such as Alzheimer's disease and for the treatment of Parkinson's disease.

13 Claims, 4 Drawing Sheets

I
S-(-)nicotine

II
(+/-)-nornicotine

III
S-(-)cotinine

IV

| A, | R=H | , X=I | (NMNI) |
| B, | R=CH$_2$CH$_3$ | , X=I | (NPNI) |
| C, | R=CH=CH$_2$ | , X=I | (NANI) |
| D, | R=(CH$_2$)$_2$CH$_3$, | X=I | (NnBNI) |
| E, | R=(CH$_2$)$_6$CH$_3$, | X=I | (NONI) |
| F, | R=C$_6$H$_5$ | , X=Br | (NBNB) |
| G, | R=CH$_2$OH | , X=I | (NHENI) |

V
(NMCI)

VI

A, R$_1$=CH$_3$, R$_2$=H    (NMNNI)
B, R$_1$=R$_2$=CH$_2$CH=CH$_2$ (DNANI)

VII
(PIPNMN)

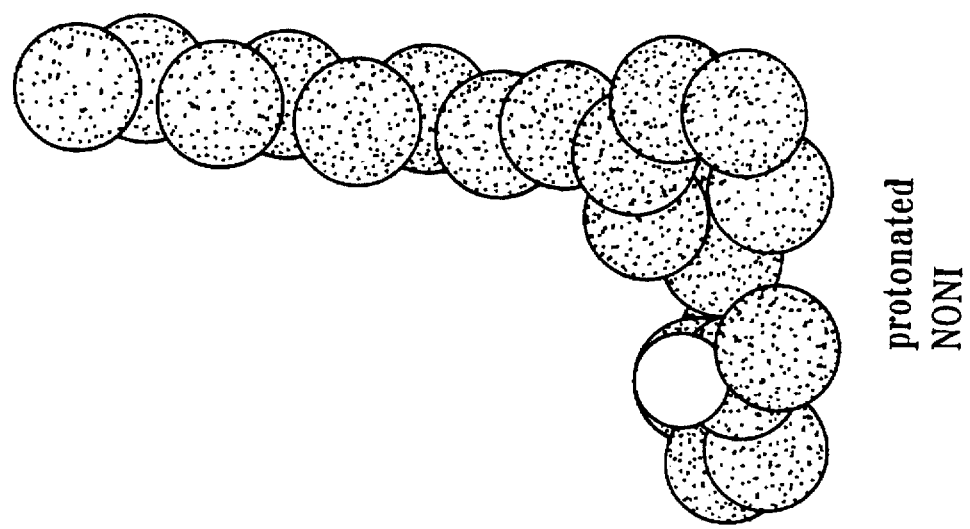
Figure 3C protonated NONI
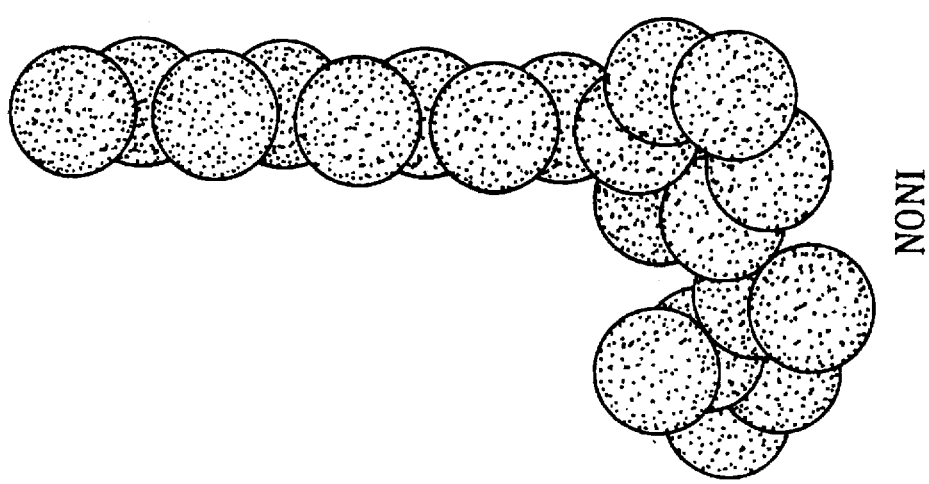
Figure 3B NONI
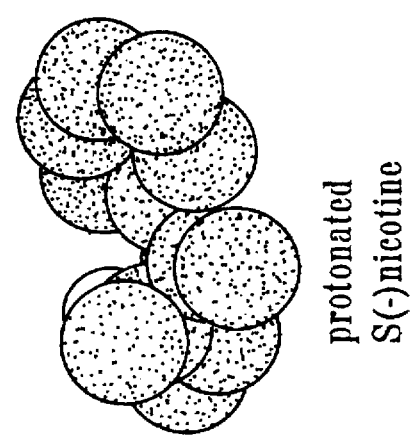
Figure 3A protonated S(-)nicotine

NICOTINIC RECEPTOR ANTAGONISTS IN THE TREATMENT OF NEUROPHARMACOLOGICAL DISORDERS

FIELD OF THE INVENTION

This invention relates to nicotine analogs that have nicotinic receptor antagonist properties. The analog compounds are shown to competitively inhibit dopamine release induced by nicotine. The nicotine analog compounds are useful in the treatment of nicotine abuse, smoking cessation therapy, as an antidote for nicotine intoxication, treatment of cognitive disorders such as Alzheimer's disease and for the treatment of Parkinson's disease.

BACKGROUND

The structure-activity relationship (SAR) of antagonist molecules at neuronal nicotinic receptors have not been systematically investigated. From the work that has been reported, there appears to be far less correlation of structure and function with antagonists than is observed with agonist molecules (Barlow and Johnson, 1989a,b; Bears and Reich, 1970; Pauling and Petcher, 1973; Sheridan et al. 1986, 1987; Wasserman et al. 1979). Due the diverse structures of antagonist molecules, it is difficult to propose a common antagonist binding site or pharmacophore for receptor antagonists such as lobeline, DHBI, neuronal bungarotoxin and strychnine. Thus, it is possible that the noncorrelation of structure and function of antagonists may reflect an antagonism at different nicotinic receptor subtypes requiring specific three dimensional antagonist pharmacophores.

Sheridan (1989) proposed that antagonists compete for the same binding site as agonists; however, antagonists may not bind in the same way as agonists. Furthermore, agonists and antagonists may bind differently to different quaternary states of the receptor protein. However, it is presumed likely from the data available that both agonists and antagonists are recognized by the anionic and donor groups in the binding site. One must assure that some property other than pharmacophore geometry must be important for antagonism. Sheridan et al. (1989) suggested that to be an agonist, a molecule must not only be able to achieve the pharmacophore geometry, but must also be confined to a specific volume.

Nicotine compounds and derivatives are known. For example, U.S. Pat. No. 4,965,074 to Leeson discloses a method for the treatment of memory impairment, especially senile dementia of the Alzheimer's type. Nicotine is one compound.

U.S. Pat. No. 5,227,391 to Caldwell et al. discloses a method of treating neuro-degenerative diseases by administering an effective amount of R(+) nicotine. U.S. Pat. No. 5,272,155 to Arneric et al. discloses a (+)2-methylpiperidine which is a specific modulator of the neuronal nicotinic cholinergic receptor and which is useful in the treatment and prevention of cognitive, neurological and mental disorders.

U.S. Pat. No. 5,278,176 to Lin discloses selective potent nicotinic agonists which are useful in the treatment of dementias, attentional hyperactivity disorder, anxiety associated with cognitive impairment, or substance abuse withdrawal. U.S. Pat. No. 5,276,043 to Lippiello et al. discloses treatment of patients suffering from negrodegenerative diseases with an effective amount of an unsaturated nicotine compound. Alzheimer's disease and Parkinson's disease are specifically mentioned as neurodegenerative disorders.

U.S. Pat. No. 5,371,188 to Heinemann et al. discloses a family of neuronal nicotinic acetylcholine receptor subunit compositions. U.S. Pat. No. 5,369,028 to Harpold et al. discloses human neuronal nicotinic acetylcholine receptor subunits.

U.S. Pat. No. 5,362,496 to Baker et al. discloses a method for treating conditions responsive to nicotine therapy, and for cessation of smoking therapy, by transmucosal administration of nicotine to a patient.

U.S. Pat. No. 5,316,759 to Rose et al. discloses a method of treating and reducing a drug dependency such as a nicotine dependency. The method involves administering nicotine in an amount that would normally provide the desired pharmacologic effects at a sustained level to partially saturate the receptors in the subject to whom nicotine is administered. An mecamylamine is administered to block the pharmacologic effects of the nicotine.

U.S. Pat. No. 5,298,257 to Bannon et al. discloses a method of treating withdrawal symptoms associated with smoking cessation with transdermal delivery of nicotine.

U.S. Pat. No. 5,232,933 to Lippiello et al. discloses treating neurodegenerative diseases with an effective amount of an alpha-nicotine type compound.

U.S. Pat. No. 5,187,169 to Lippiello et al. discloses methods of treating neurodegenerative disorders such as Alzheimer's disease and Parkinson's disease with an effective amount of a cotinine compound.

U.S. Pat. No. 5,069,904 to Masterson discloses a method of using nicotine in the treatment of conditions susceptible to such treatment. Such conditions include disease states characterized by reduced central cholinergic function. Nicotine is administered to the subject until a therapeutic dose is achieved.

*NeuroReport*, Vol. 3, No. 12, pp. 1117–1120, December 1992, discloses chronic nicotine treatment decreases dopamine 2 agonist binding in rat basil ganglia.

*The European Journal of Pharmacology*, Vol. 173, No. 1, pp. 93–108, Nov. 28, 1989, set out to determine whether N-methylcarbicol acts as an agonist or antagonist at nicotine and/or muscarinic receptor sites. Nicotine stimulates the release of [3H]dopamine from rat striatal synaptosomes pre-loaded with dopamine.

*The Journal of Neurochemistry*, Vol. 46, No. 4, pp. 1109–17, April 1986 discloses that acetylcholine and nicotine accelerated the basil outflow of gamma-aminobutyric acid (GABA) from rabbit caudate nucleus. The findings indicate that the GABA neurons and the caudate nucleus may be stimulated by dopamine and stimulated by acetylcholine via a nicotine receptor.

*The Journal of Neurochemistry*, Vol. 40, No. 4, pp. 1106–9, April 1983 discloses that tetrodotoxin-sensitive $Na^+$ channels block nicotine transmission, possibly by noncompetitively inhibiting the interaction of nicotine with the receptor binding site.

*Biochemistry*, Vol. 19, No. 12, pp. 2770–9, Jun. 10, 1980, describes the quantitative analysis of nicotine acetylcholine receptor function in torpedo postsynaptic membranes.

*Biochemistry Soc. Symp.*, Vol. 59, pp. 83–95, 1993, discloses a view among researchers and clinicians that habitual cigarette smoking is a form of dependence on nicotine. It is the central action of nicotine that appears to be particularly important in this regard. Although multiple subtypes of nicotine receptor are expressed in the brain, attention has focused on a prevalent subtype (containing alpha 4 and beta 2 subunits) which is believed to represent the prime target for "smoking doses" of nicotine. The mesolimbic dopamine system, a neuronal population which has been implicated in the reinforcing actions of certain drugs (e.g. amphetamine), also appears to mediate the reinforcing actions of nicotine in laboratory rats. Pharmacotherapeutic approaches to smoking cessation rely on nicotine replacement. This publication argues that the administration of a selective antagonist of central nervous system nicotine receptors may lead to higher long-term abstinence rates, and research strategies for the development of such a drug are outlined.

*The Journal of Substance Abuse*, Vol. 1, No. 3, pp. 259–71, 1989, describes dealing with the molecular features of nicotine, the receptor binding and psychotropic properties of nicotine agonists and antagonists, and the neuroanatomical locus of action of nicotine associated with its psychotropic action. Bridged analogues of nicotine have been developed to define the optimal conformation of the molecule for maximal receptor affinity and psychotropic action in rats. With another series of analogues, it was demonstrated that contraction of the pyrrolidine ring to a 4-member azetidine enhances potency while expansion diminishes it. A major site for nicotine's central action is the vestibular cerebellum as demonstrated by kainic acid lesioning studies and direct administration of nicotine into this region. Included among the antagonists to nicotine was alpha-lobeline, which appeared to be a mixed agonist-antagonist.

*Neuroendocrinology*, Vol. 47, No. 4, pp. 303–8, April 1988, discloses the effect of cholinergic agonists and antagonists on rat hypothalamic and corticotropin-releasing hormone secretion in vitro. Acetylcholine (ACh) stimulated hypothalamic IR-rCRH secretion in a dose-dependent fashion, at concentrations ranging from 3.3×10(−10) to 10(−5)M. This effect was antagonized by the simultaneous presence of atropine and hexamethonium, a muscarinic and a nicotinic receptor antagonist, respectively (p less than 0.05). Further evidence for the cholinergic regulation of the CRH neuron was provided by the findings that both carbachol, a muscarinic receptor agonist, and nicotine, a nicotinic receptor agonist, stimulated IR-rCRH secretion in a dose-dependent fashion. These effects were antagonized by atropine and hexamethonium, respectively, suggesting that both muscarinic and nicotinic receptors are involved in the process.

The nicotine analogs of the present invention have not been disclosed by any prior art and unexpectedly have different properties than known compounds. The present nicotine analogs that have nicotinic receptor antagonist properties. The analog compounds are shown to competitively inhibit dopamine release induced by nicotine. The nicotine analog compounds overcome the deficiencies of prior art compounds and are useful in the treatment of nicotine abuse, smoking cessation therapy, as an antidote for nicotine intoxication, treatment of cognitive disorders such as Alzheimer's disease and for the treatment of Parkinson's disease.

DISCLOSURE OF THE INVENTION

The invention provides compounds of the following formula:

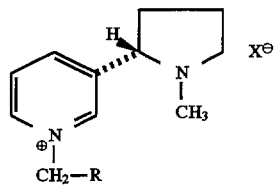

wherein R=N-alkyl or branched alkyl with 2–19 carbon atoms, cycloalkyl, aralkyl, N-alkenyl or alkenyl with 2–19 carbon atoms, and N-alkynyl or branched alkynyl with 2–19 carbon atoms. X=Cl$^-$, Br$^-$, I$^-$, HSO$_4^-$, ½SO$_4^{2-}$. These compounds are useful in the treatment of nicotine abuse, smoking cessation therapy, as an antidote for nicotine intoxication, treatment of cognitive disorders such as Alzheimer's disease and for the treatment of Parkinson's disease.

It is another object of the invention to provide compounds having nicotinic receptor antagonist properties.

In a preferred embodiment the invention provides A method of antagonizing the nicotinic receptor comprising administering a pharmaceutically effective amount of a compounds of the invention.

In still another embodiment the invention provides a method of treatment of nicotine abuse, as smoking cessation therapy, as an antidote for nicotine intoxication comprising administering a pharmaceutically effective amount of a compound according to the invention.

Advantageously the invention provides a method of treatment of treatment of cognitive disorders selected from the group consisting of Alzheimer's disease and Parkinson's disease comprising administering a pharmaceutically effective amount of a compound according to the invention.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE DRAWINGS

FIG. 3 shows space filling models of minimum energy conformers of N'-protonated S(−)nicotine and the unprotonated and protonated forms of NONI.

DESCRIPTION OF THE INVENTION

Figure 1A:
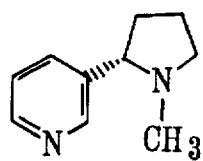
FIG. 1 shows structures of S(−)nicotine and related compounds studied in [$^3$H]DA release assays. Abbreviated nomenclature is given in parentheses.
Figure 1B:
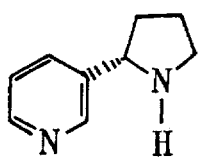
Figure 1C:
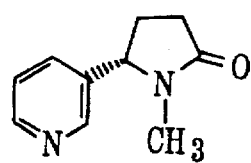
Figure 1D:
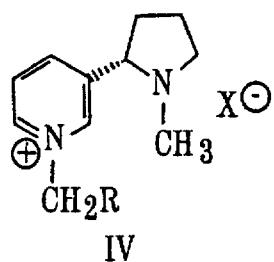
Figure 1E:
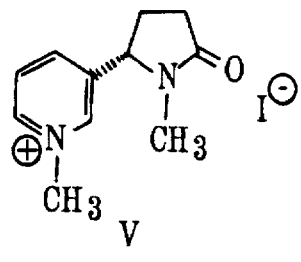
Figure 1F:
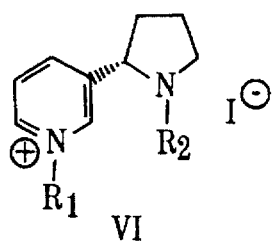
Figure 1G:
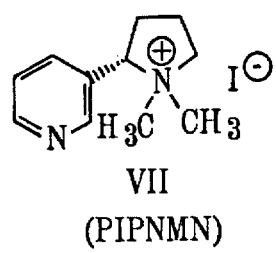

The present nicotine analogs have nicotinic receptor antagonist properties. The analog compounds are shown to competitively inhibit dopamine release induced by nicotine. The nicotine analog compounds overcome the deficiencies of prior art compounds and are useful in the treatment of nicotine abuse, smoking cessation therapy, as an antidote for nicotine intoxication, treatment of cognitive disorders such as Alzheimer's disease and for the treatment of Parkinson's disease.

Hybridization cloning has revealed a surprising degree of subtype diversity among neuronal nicotinic receptors (Leutje et al. 1990a; Deneris et al. 1991); Role, 1992; Sargent, 1993). There are two types of neuronal nicotinic subunits α and β. The α subunits are identified by a pair of adjacent cysteine residues in the amino terminal domain and are traditionally thought of as the agonist-binding subunit. Eight subtypes of the α subunit (α2-α9) and three subtypes of the β subunit (β2-β4) have been found in the vertebrate nervous system. The functional significance of this subtype diversity is still a mystery.

Both native and cloned subtypes are pharmacologically distinct in their response to both nicotinic agonists and antagonists. In terms of antagonists, α-bungarotoxin (α-BTX) selectively blocks receptors that contain the α7, α8, or α9 subunits, and neuronal bungarotoxin (NBTX) selectively blocks the α3β2 receptor (Leutje et al. 1990b). However, there are no selective toxins for receptors that contain the α2, α4, or β4 subunits.

Nicotine activates presynaptic neuronal nicotinic receptors evoking the release of dopamine (DA) from presynaptic terminals in the central nervous system (Giorguieff-Chesselet et al. 1979; Westfall et al. 1993; Rowell et al. 1987; Rapier et al. 1988, 1990; Grady et al. 1992). The specific nicotinic receptor subtype which mediates nicotine-evoked DA release has not been directly identified, but has been suggested to be the α3β2 subtype (Schulz et al. 1989; Grady et al. 1992). Developing subtype-selective antagonists are particularly important, because there are no selective toxins for receptors that contain the α2, α4, or β4 subunits. Furthermore, development of subtype selective antagonists for the α3β2 subtype is important, because NBTX is practically unavailable due to export restrictions on the source snakes.

The invention relates to the development of novel nicotinic antagonists which inhibit nicotine-evoked dopamine release from rat striatal slices, with selectivity at the α3β2 neuronal nicotinic receptor subtype.

A series of N-substituted nicotine analogues were synthesized and evaluated for their ability to inhibit nicotine-evoked [$^3$H]dopamine([$^3$H]DA) release from rat striatal slices. Of the eleven compounds examined, the most efficacious analogues were those that contained a pyridino N-alkyl substituent of three carbons or more in length. Structure-activity relationships indicate that the order of potency correlated with increase in alkyl chain length. Introduction of an aromatic or unsaturated residue into the pyridino-N substituent also afforded compounds with significant antagonist activity. The most efficacious and potent compound in the series was S-N-octylnicotinium iodide (NONI).

NONI had a potency approximately half that of the classical nicotinic antagonists, mecamylamine and dihydro-β-erythroidine (DHBE). Moreover, NONI completely blocked the effect of nicotine to evoke [$^3$H]DA release, whereas the classical antagonists inhibited but did not completely block nicotine's effect. Furthermore, NONI did not possess agonist activity at concentrations which completely blocked nicotine-evoked [$^3$H]DA release. The pKa values determined for S(−)nicotine and one of the most active antagonists, S-N-allyl-nicotinium iodide (NANI), shows that these analogues exist predominantly in their unprotonated form at physiological pH.

Molecular modeling studies suggest that these antagonists may interact with the nicotinic receptor in a novel binding mode which is different from the mode of interaction of nicotine with this receptor. This structure-activity data provides useful information on the antagonist pharmacophore of the nicotine receptor subtype responsible for modulation of dopamine release from presynaptic terminals in the brain. Thus, it is proposed that these antagonists bind to the receptor in their unprotonated forms and that the binding mode involves interaction of the quaternary pyridinium-N atom with the anionic site of the receptor. The unprotonated pyrrolidine-N atom serves as the hydrogen bond acceptor, which reverses the roles the nitrogens normally play in the binding of nicotine to the receptor. The N-alkyl substituent most likely binds to a site that extends beyond the normal agonist pharmacophore volume which may prevent the receptor protein from achieving its open-channel quaternary form.

Thus, a new class of efficacious nicotinic antagonists have been discovered which inhibit nicotine evoked [$^3$H]DA release from dopaminergic nerve terminals in the brain providing new tools for unraveling the role of neuronal nicotinic receptors modulating dopamine release. A description of synthesis methods for these compounds, their pharmaceutical formulations and their methods of use are set forth below.

EXAMPLE 1

Synthesis. Several N-substituted analogues of S(−) nicotine (I), S(−)cotinine (II) and racemic nornicotine (III) were prepared (FIG. 1 and Table 1) and evaluated for their ability to act as antagonists at neuronal nicotinic receptors (Tables 2 and 3). Compounds IVA-G were synthesized via direct alkylation of the pyridine-N atom of S(−)nicotine following a modification of the method reported by Shibagaki et al. (1982). Compound V was synthesized by the method of McKennis et al. (1963), and compound VII was synthesized using a modification of the method employed by Seeman and Whidby (1976). Compound VIA was prepared from racemic nornicotine via the reported method of Pool (1987). Compound VIB was prepared by reaction of racemic nornicotine with allyl iodide (Table I). All products were characterized by elemental analysis which afforded values that did not deviate by ±0.40% of theoretical values, and by $^1$H-NMR. The $^1$H-NMR spectra of compounds IVA-G were consistent with alkylation occurring at the pyridine-N atom rather than at the pyrrolidine-N atom, as indicated by the downfield chemical shift values for the aromatic protons compared to the values for the same protons of nicotine. The pyrrolidine N-methyl group exhibited a similar chemical shift (approximately 2.3 ppm) for the NCH$_3$ singlet in both nicotine and nicotine analogues IVA-G. Synthetic and analytical data for the above compounds is provided in Table 1.

TABLE 1

Synthetic and analytical data for N-substituted nicotine analogues

| Compound[a] | | R | X | Reaction Solvent | Reaction Temperature | Reaction Time | Purification[b] | % Yield | Melting Point (°C.) |
|---|---|---|---|---|---|---|---|---|---|
| S-IVa | NMNI | H | I- | AcOH | reflux | 12 h | A | 75 | 165–166 |
| S-IVb | NPNI | $CH_2CH_3$ | I- | AcOH | ambient | 48 h | B | 56 | 83–84 |
| S-IVC | NANI | $CH=CH_2$ | I- | AcOH | ambient | 48 h | B | 64 | 88–90 |
| S-IVd | NnBNI | $(CH_2)_2CH_3$ | I- | MeOH | +55° C. | 48 h | chromatogr. | 40 | 81–82 |
| S-Ve | NONI | $(CH_2)_6CH_3$ | I- | MeOH | +55° C. | 48 h | B | 20 | oil |
| S-IVf | NBNB | $C_6H_5$ | Br- | AcOH | +55° C. | 24 h | B | 65 | 159–160 |
| S-IVg | NHENI | $CH_2OH$ | I- | MeOH | +55° C. | 48 h | chromatogr. | 55 | hygroscopic |
| S-V | NMCI | — | I- | MeOH | +50° C. | 3 h | C | 79 | 147–148 |
| (±)VIa | NHNNI | $R1=CH_3;R2=H$ | I- | AcOH | ambient | 24 h | D | 67 | 207–209 |
| (±)VIb | DNANI | $R1=R2=CH_2CH=CH_3$ | I- | THF | ambient | 24 h | B | 55 | 123–124 |
| S-VII | PIPNNN | — | I- | MeOH | ambient | 24 h | D | 60 | 135–137 |

[a]See Figure 1 for structures of compounds.
[b]Method of Purification: A, After evaporation of the solvents and addition of saturated $NaHCO_3$, the basic solution (pH = 8) was washed with ether before extraction with chloroform. B, Column chromatography over silica gel elution with 5% MeOH in chloroform. C, Recrystalization from MeOH. D, Preparative cation-exchange HPLC.

pKa Determination. A solution [1 g in 12 mls of deuterium oxide 100% atom D] of the compound under investigation was gradually acidified by drop-wise addition of a solution of DC1 to $D_2O$ (20% wt/wt, 99.5% atom D). The pD values were measured on a Corning pH meter. For each pD value, a sample (0.8 mls) was analyzed by $^1$H-NMR on a Varian Unity 300 MHz spectrometer using sodium 3(trimethylsilyl)-2,2,3,3-$d_4$-propionate (TSP) as internal reference. Protonation of the pyrrolidine- and pyridine-N atoms was followed by observing the variation in chemical shift of the N-1'-methyl and 2'-proton signals from pO 8.8 to pD 3.0. A titration curve of pD vs chemical shift was constructed to determine the pKa values of pyrrolidino-N atom and/or the pyridine-N atom.

Computational Chemistry. A solution [1 g in 12 mls of deuterium oxide 100% atom D] of the compound under investigation was gradually acidified by drop-wise addition of a solution of DC1 to $D_2O$ (20% wt/wt, 99.5% atom D). The pD values were measured on a Corning pH meter. For each pD value, a sample (0.8 mls) was analyzed by $^1$H-NMR on a Varian Unity 300 MHz spectrometer using sodium 3-(trimethylsilyl)-2,2,3,3-$d_4$-propionate (TSP) as internal reference. Protonation of the pyrrolidine- and pyridine-N atoms was followed by observing the variation in chemical shift of the N-1'methyl and 2'-proton signals from pD 8.8 to pD 3.0. A titration curve of pD vs chemical shift was constructed to determine the pKa values of pyrrolidino-N atom and/or the pyridine-N atom.

Computational Chemistry. The molecular modeling package HYPERCHEM© (AutodesK, Inc. California) was used to calculate energy-minimized conformers of protonated and unprotonated molecules. Partial charges were calculated using External Hückel Methods, and structures were minimized with the MM+ molecular mechanics force field, using Polak-Ribiere as the minimization algorithm., Biological Methods. Male Spragua-Dawley rats (150–200 g) were obtained from Harlan Laboratories (Indianapolis, Ind.) and were housed two per cage with free access to food and water in the Division of Lab Animal Resources at the College of Pharmacy at the University of Kentucky. Experimental protocols involving the animals were approved by the Institutional Animal Care and Use Committee at the University of Kentucky.

[$^3$H]DA Release Assay. Rat striatal slices (500 μm thickness, 6–8 mg wet weight) were obtained as previously described (Dwoskin and Zahniser, 1986). Slices were incubated for 30 min in Krebs' buffer (in nM; 118 NaCl, 4.7 KCl, 1.2 $MgCl_2$, 1.0 $NaH_2PO_4$, 1.3 $CaCl_2$, 1.3 $CaCl_2$, 11.1 glucose, 25 $NaHCO_3$, 0.11 L-ascorbic acid nd 0.004 disodium EDTA; pH 7.4 and saturated with 95% $O_2$/5% $CO_2$) in a metabolic shaker at 34°. Slices were rinsed with 15 ml of fresh buffer and incubated for an additional 30 min in fresh buffer containing 0.1 μM [$^3$H]dopamine (6 slices/3 ml). Subsequently, slices were rinsed with 15 ml of fresh buffer and transferred to a glass superfusion chamber. Slices were superfused (1.0 ml/min) for 60 min with Krebs' buffer containing nomifensine (10 μm) and pargyline (10 μm) and maintained at 34° C., pH 7.4 with continual aeration (95% $O_2$/5% $CO_2$). Two 5-min samples (5 ml) were collected to determine basal outflow of [$^3$H]DA. N-Substituted nicotine analogues were added to the superfusion buffer after the collection of the second sample and remained in the buffer until 12 consecutive 5-min samples were collected. Subsequently, S(−)nicotine (10 μM) was added to the buffer and an additional 12 consecutive 5-min samples were collected. At the end of the experiment each slice was solubilized and the [$^3$H] content of the tissue determined.

Radioactivity in the superfusate and tissue samples was determined by liquid scintillation spectroscopy. Fractional release for each superfusate sample was calculated by dividing the total tritium collected in each sample by the total tritium present in the tissue at the time of sample collection. Basal [$^3$H]out flow was calculated from the average of the tritium collected in the two 5-min samples just before addition of the N-substituted nicotine analogue. The sums of the increase in collected tritium resulting from either exposure to the test compound or exposure to nicotine in the absence and presence of the test compound equaled total [$^3$H]overflow. [$^3$H]overflow was calculated by subtracting the [$^3$H]outflow during an equivalent period of prestimulation from the values in samples collected during and after drug exposure. Inasmuch as the radiolabelled compounds were not separated and identified, the tritium collected in superfusate is referred to as either [$^3$H]outflow or [$^3$H]overflow, rather than as [$^3$H]DA. [$^3$H]Overflow primarily represents [$^3$H]DA in the presence of nomifensine and pargyline in the superfusion buffer (Zumstein et al. 1981).

The effects of the nicotinic agonist, S(−)nicotine, and two of its metabolites, S(−)cotinine and (±)nornicotine, on [$^3$H] DA release from rat striatal slices are shown in Table 2.

TABLE 2

TABLE 2. The effect of S(−)nicotine, S(−)cotinine, S(−)cytisine and racemic nornicotine on [$^3$H]DA release from rat striatal slices

| Compound | N[a] | Concentration (µM) | | |
|---|---|---|---|---|
| | | 1 | 10 | 100 |
| S(−)nicotine | 9 | 2.80 ± 0.28[b] | 3.24 ± 0.37 | 5.56 ± 0.50 |
| S(−)cystisine | 5 | 0.67 ± 0.26 | 0.85 ± 0.38 | 1.13 ± 0.46 |
| S(−)cotinine | 6 | 0 ± 0 | 1.14 ± 0.36 | 2.06 ± 0.35 |
| (±)nornicotine | 8 | 1.40 ± 0.24 | 2.60 ± 0.38 | 4.20 ± 0.34 |

[a]N = number of animals.
[b]Data are expressed as total [$^3$H]overflow, mean ± S.E.M.

The effect of the high affinity nicotinic ligand, S(−) cytisine, was also evaluated for its ability to release [$^3$H]DA from striatal slices. From these data, S(−)nicotine produced a concentration-dependent increase in [$^3$H]DA release and was the most potent and efficacious compound compared to the other agonists studied. Racemic nornicotine also produced a concentration-dependent increase in [$^3$H]DA release, but evoked release which was only 50% of the effect produced by S(−)nicotine at 1 µM, and approximately 80% of that at the higher concentrations. The effect of racemic nornicotine was compared with that of S(−)nicotine because of the reported lack of stereoselective effect of nornicotine (Reavill et al. 1988; Copeland et al. 1991; Risner et al. 1985, 1988; Goldberg et al. 1989) and due to the difficulty in obtaining enatiomerically pure forms of nornicotine. Cotinine, the major metabolite of nicotine, had no effect at 1 µM, and only produced a small effect (35% of nicotine's effect) at the higher concentrations.

The N-substituted nicotine analogues described in Table 1 were evaluated for their ability to evoke [$^3$H] release from rat striatal slices at three concentrations (1, 10 and 100 µM) (Table 3).

TABLE 3

The effect of DHBE, MEC and N-substituted nicotine analogues on [$^3$H]DA release from rat striatal slices

| Compound | N[a] | Concentration (µM) | | | |
|---|---|---|---|---|---|
| | | 0 | 1 | 10 | 100 |
| NONI | 6 | 0.01 ± 0.01[b] | 0.03 ± 0.02 | 0.14 ± 0.14 | 16.4 ± 2.00 |
| DHBE | 5 | 0.00 ± 0.00 | 0.02 ± 0.02 | 0.36 ± 0.22 | 2.01 ± 0.28 |
| MEC | 4 | 0.00 ± 0.00 | 0.00 ± 0.00 | 0.00 ± 0.00 | 0.00 ± 0.00 |
| NBNB | 7 | 0.05 ± 0.05 | 0.21 ± 0.12 | 0.28 ± 0.12 | 6.04 ± 0.97 |
| NPNI | 8 | 0.00 ± 0.00 | 0.06 ± 0.01 | 0.03 ± 0.03 | 0.03 ± 0.03 |
| NnBNI | 5 | 0.00 ± 0.00 | 0.00 ± 0.00 | 0.01 ± 0.01 | 0.01 ± 0.01 |
| NANI | 9 | 0.00 ± 0.00 | 0.02 ± 0.02 | 0.07 ± 0.04 | 0.08 ± 0.03 |
| NHENI | 6 | 0.10 ± 0.07 | 0.00 ± 0.00 | 0.00 ± 0.00 | 0.08 ± 0.04 |
| (±) DNANI | 5 | 0.02 ± 0.01 | 0.02 ± 0.01 | 0.08 ± 0.04 | 0.00 ± 0.00 |
| (±) NMNNI | 5 | 0.00 ± 0.00 | 0.17 ± 0.11 | 0.01 ± 0.01 | 2.60 ± 0.38 |
| NMNI | 5 | 0.02 ± 0.01 | 0.13 ± 0.11 | 0.17 ± 0.10 | 0.08 ± 0.06 |
| NMCI | 5 | 0.00 ± 0.00 | 0.00 ± 0.00 | 0.01 ± 0.01 | 0.02 ± 0.01 |
| PIPNMN | 4 | 0.00 ± 0.00 | 0.03 ± 0.03 | 0.01 ± 0.01 | 0.05 ± 0.02 |

N[a] = number of animals.
[b]Data are expressed as total [$^3$H] overflow, mean ± S.E.M.

In addition, the classical competitive and noncompetitive nicotinic antagonists, DHBE (Vidal and Changeux, 1989; Alkondon and Albuquerque 1991; Mulle et al. 1991) and mecamylamine (Grenhoff and Svensson, 1989; Mulle et al. 1991) were also examined in this assay for the sake of comparison. None of the compounds examined, including DHBE and mecamylmine, had any significant effect on [$^3$H]DA release in the concentration range of 1–10 µM. However, at the highest concentration (100 µM) examined, HONI, NBNB, and (±)NMNNI evoked [$^3$H]DA release and thus, possess intrinsic agonist activity at this concentration. In particular NONI was quite efficacious and exhibited three-times the agonist activity of nicotine at the 100 µM concentration. At this high concentration, DHBE also evoked [$^3$H]DA release (Table 3).

The N-substituted nicotine analogues were evaluated for their ability to inhibit nicotine-evoked [$^3$H]DA release (Table 4).

TABLE 4

N-Substituted nicotine analogue-induced antagonism of S(−)nicotine (10 µM)-evoked [$^3$H]DA release from rat striatal slices

| Compound | N[a] | Concentration (µM) | | | |
|---|---|---|---|---|---|
| | | 0[c] | 1 | 10 | 100 |
| NONI | 6 | 1.84 ± 0.20[b] | 1.21 ± 0.14 | 0.03 ± 0.02 | ND[d] |
| DHBE | 5 | 3.10 ± 0.60 | 1.59 ± 0.09 | 0.73 ± 0.12 | ND |
| MEC | 4 | 2.64 ± 0.84 | 0.87 ± 0.18 | 0.68 t 0.23 | 0.41 ± 0.31 |
| NBNB | 7 | 2.98 ± 0.51 | 1.50 ± 0.55 | 1.27 ± 0.35 | ND |
| NPNI | 8 | 2.06 ± 0.45 | 1.63 ± 0.41 | 0.88 ± 0.51 | 0.31 ± 0.13 |
| NnBNI | 5 | 2.29 ± 0.41 | 2.70 ± 0.52 | 1.03 ± 0.28 | 0.39 ± 0.09 |
| NANI | 9 | 1.96 ± 0.29 | 2.61 ± 0.46 | 0.92 ± 0.35 | 0.48 ± 0.18 |
| NHENI | 6 | 2.45 ± 0.40 | 1.66 ± 0.10 | 2.13 ± 0.38 | 0.34 ± 0.11 |
| (±) DNANI | 5 | 1.94 ± 0.39 | 2.58 ± 0.54 | 1.85 ± 0.25 | 1.66 ± 0.36 |
| (±) NMNNI | 5 | 2.97 ± 0.48 | 2.22 ± 1.26 | 3.53 ± 0.85 | ND |
| NMNI | 5 | 1.94 ± 0.29 | 2.10 ± 0.81 | 3.33 ± 1.27 | 1.65 ± 0.90 |
| NMCI | 5 | 2.97 ± 0.48 | 3.11 ± 1.32 | 3.11 ± 1.20 | 3.75 ± 1.66 |
| PIPNMN | 4 | 3.07 ± 0.61 | 3.16 ± 1.46 | 2.98 ± 1.48 | 1.88 ± 0.77 |

N[a] = number of animals.
[b]Data are expressed as total [$^3$H]overflow, mean ± S.E.M. during co-superfusion with 10 µM nicotine.
[c]Nicotine (10 µM)-evoked total [$^3$H]overflow determined for each experiment. Grand mean was 2.52 ± 0.12 with a range of 1.03–4.65 for N = 82 separate experiments.
[d]ND indicates not determined as a result of intrinsic agonist activity.

Figure 2:
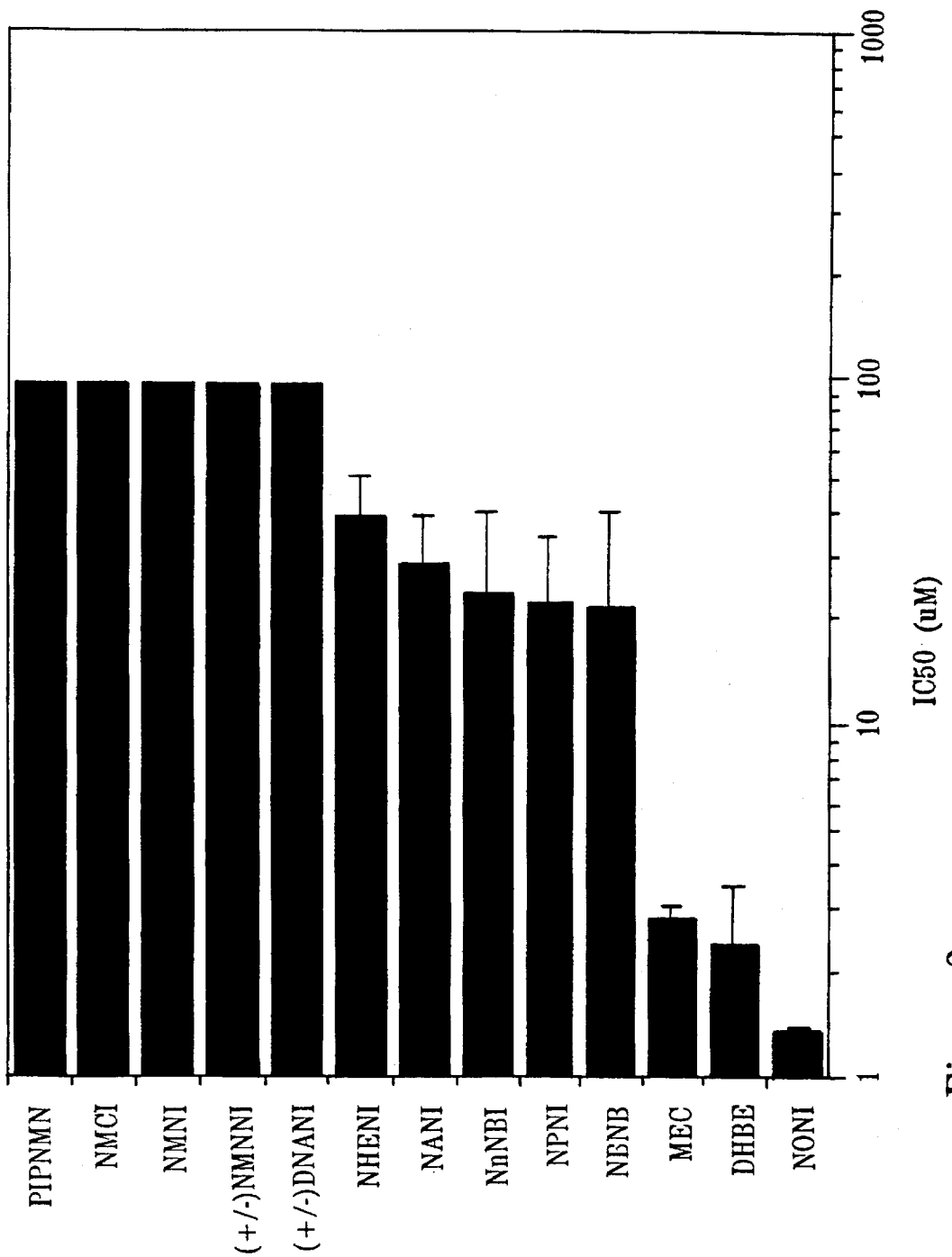
FIG. 2 shows IC50 values for N-substituted analogues of nicotine, nornicotine, and cotinine to inhibit nicotine-evoked [$^3$H]DA release from rat striatal slices.

In these experiments, the striatal slices were superfused for 60 min with various concentrations of the analogues prior to nicotine (10 µM) exposure. Antagonist activity was evaluated by comparing the nicotine-evoked [$^3$H]overflow in the absence and presence of the analogues. From the group of quaternary ammonium analogues examined, PIPNMN, NMCI, NMNI, (±)NMNNI, and (±)DNANI did not exhibit significant nicotinic antagonist activity over the concentration range tested. However, it should be noted that two of these inactive compounds are racemates. Significant antagonist activity was observed with NHENI, NANI, NnBNI, NPNI, NBNB and NONI. The relative order of potency of the classical and pyridine-N substituted nicotine analogues for inhibition of nicotine-evoked [$^3$H]DA release from rat striatal slices is illustrated in FIG. 2 by a comparison of their IC50 values. The order of potency wherein NONI>>DHBE= MEC>>NBNB=NPNI=NnNBI=NANI>NHENI>>>(±)di-N-allyl nicotinium iodide (DNANI)=(±)N-methyl nornicotinium iodide (NMNNI)=NMNI=S-N-methyl cotininium iodide (NMCI)=S-N'-methyl nicotinium iodide (PIPNMN).

The most potent and efficacious antagonist in this series of analogues was clearly NONI (Table 4 and FIG. 2). At the low concentration of 10 µM, NONI completely inhibited nicotine-evoked [$^3$H]DA release. Furthermore, NONI was 16-fold more effective than DHBE and MEC at this concentration. However, the NONI-induced inhibition of the effect of nicotine could not be determined at the 100 µM, since similar to DHBE, NONI possessed intrinsic agonist activity at this high concentration. It is important to note, however, that the intrinsic agonist activity of NONI was observed at a concentration 10-fold higher than that required to completely inhibit nicotine-evoked [$^3$H]DA release.

Determination of the pKa value of the pyrrolidino-N functionality of NANI by $^1$H-NMR analysis afforded a value of 6.4 This value for NANI was considerably lower than the pKa value of 8.4 for the same functionality in the nicotine molecule when analyzed in an identical manner. The pyridine-N functionality of nicotine afforded a pKa value of 3.75. These results indicate that at physiological pH (7.6) the quaternary nicotine analogues exist predominantly in their unprotonated forms whereas, nicotine exists predominantly in its N-1' protonated form. Thus, both molecules are monocationic at physiological pH, but the positive charge in the respective molecules is located on different nitrogen atoms.

Conformational analysis data for nicotine and the three most effective antagonists provides information on the energy-minimized conformations of the protonated and unprotonated forms of these compounds (Table 5).

TABLE 5

Table 5. Characteristics of minimized energy conformations for S(−)nicotine and the S(−)quaternary ammonium analogues of nicotine

| Compound | N—N' Intra-atomic Distance (Angstroms) | C(3)-C(2') Torsion Angle (Degrees) |
|---|---|---|
| Nicotine | | |
| free base | 4.35 | 109.8 |
| monoprotonated (N$^+$H) | 4.19 | 113.2 |
| diprotonated | 4.70 | 117.0 |
| NBNB | | |
| monocation | 4.04 | 112.2 |
| dication (N$^+$H) | 4.90 | 115.7 |
| NANI | | |
| monocation | 4.00 | 111.4 |
| dication (N$^+$H) | 4.81 | 117.7 |
| NONI | | |
| monocation | 4.08 | 111.2 |
| dication (N$^+$H) | 4.70 | 116.8 |

As expected, generation of a dicationic species of these compounds results in a significant change in the N-N' intra-atomic distance as compared to the monocationic species. This is due to the charge repulsion between the two positive nitrogen centers, which induces a significant rotation about the C(3)-C(2') bond. Since the NMR data indicates that it is predominantly the monocationic form of the antagonist that exists at physiological pH, it is likely that this is the form that interacts with the nicotinic receptor. It is interesting to note that the N-N' intra-atomic distance and the C(3)-C(2') torsion angle value for the monocationic (i.e., unprotonated) forms of the antagonist molecules corresponds quite closely to the same values for the monoprotonated S(−)nicotine species.

As has been previously reported (Giorguieff-Chesselet et al. 1979; Westfall et al. 1983; Rowell et al. 1987; Rapier et al. 1988, 1990; Grady et al. 1992; Dwoskin et al. 1993), nicotine and nornicotine evoked a concentration-dependent increase in [$^3$H]DA release from rat striatal slices; however, nornicotine was less potent in producing this effect. In the current study, the EC50 value for nicotine was=2 µM, which is within the wide range of EC50 values (10 nM–10 µM) reported by others (vide supra) using various preparations and nicotine exposure times.

S(−)Cotinine, the major metabolite of S(−)nicotine detected in brain (Petersen et al. 1984); Stalhandske, 1970) had little effect even at high concentrations in the DA release assay. Interestingly, the high affinity ligand S(−)cytisine only marginally released dopamine from the striatal slice, producing approximately 20% of the effect of nicotine at each concentration examined in the present study. These results are in agreement with others (El-Bizri and Clarke, 1994) reporting a lesser effect of cytisine compared to nicotine in evoking dopamine release from rat striatal synaptosomes. The results suggest that the nicotinic receptor subtype modulating DA release may be different from nicotinic receptor subtype(s) that avidly bind [$^3$H]nicotine and [$^3$H]cytisine.

Unexpectedly, DHBE, the competitive nicotinic antagonist, evoked [$^3$H]DA release at the highest concentration examined (Table 3). This effect has not been previously reported. It is doubtful whether concentrations of DHBE as high as 100 µM have physiological relevance in vivo. Nevertheless, this concentration of DHBE is used routinely for nicotinic receptor antagonism in in vitro pharmacological studies (Grady et al. 1992; El-Bizri and Clarke, 1994).

From structure-activity considerations of the series of nicotine analogues examined, it is evident that quaternization of the pyridine-N atom of S(−)nicotine can result in compounds that possess antagonist activity in the nicotine-evoked [$^3$H]DA release assay. Greatest antagonist potency was obtained with an pyridine-N substituent (NONI) bearing eight carbons in a linear chain. Smaller carbon chains (two to five) had significantly lower potency and efficacy (i.e., NANI, NPNI, NnBNI, and NBNB). Consistent with this trend in structure activity is the finding that introduction of a sterically small pyridine-N substituent affords an analogue, NMNI which exhibits no antagonistic activity. Similarly, pyridino-N-methylation of both S(−)continine and (±)nornicotine also afforded compounds (NMCI and NMNI, respectively) which were devoid of antagonist activity. Pyridine-N quaternization of a nicotine analogue in which the pyrrolidine-N-methyl group has been substituted by a larger alkyl group (i.e., N-allyl, see (±)DNANI) results in relatively weak antagonist activity compared to the N-allyl nicotine analogue (NANI).

Introduction of unsaturated or aromatic moieties into the pyridine-N substituent structure also results in compounds possessing antagonist activity (e.g., NANI nd NBNB, respectively). Thus, a relatively-long, linear, alkyl chain representing a substituent that is lipophilic in nature appears to be an important determinant of antagonist activity in these quaternary ammonium analogues of nicotine. Antagonists are almost always large molecules, which, if docked onto the agonist, would extend outside the normal against volume. Thus, the extra bulk associated with the antagonist structures may prevent the receptor protein from achieving the open-channel quaternary form.

The inventors show the molecules described are binding to the antagonist site in their unprotonated forms and that the binding mode involves interaction of the quaternary ammonium nitrogen with the anionic site of the receptor. The unprotonated tertiary amine (i.e. the pyrrolidine N) interacts with the hydrogen-bond donor site. This is the reverse of the normal binding mode of an agonist such as nicotine (FIG. 3). The pKa values for the quaternary nicotine analogues is in accord with this hypothesized mode of binding, since it clearly indicates that the most predominant species of the quaternary ammonium nicotine analogue at physiological pH is the unprotonated form; whereas in the case of S(−) nicotine, the most predominant form at this pH would be the pyrrolidine-N protonated form. The locus of positive charge is thus switched from one nitrogen to the other in these two structures.

The molecular modeling data on the three most active antagonists NANI, NONI and NBNB, provide the two pH-dependent, energy-minimized conformations in aqueous solution. The unprotonated species of NONI, the most active antagonist, in which the N-N' atomic distance is about 4.0 A is illustrated in FIG. 3. The N'-protonated species of this compound (FIG. 3) has an N-N' atomic distance which is significantly greater than 4.0 A in its preferred conformation. This increase in intra-atomic N distance, which is most likely a result of ion repulsion between the two cationic centers, is equivalent to a rotation of approximately 8° about the C(3)-C(2') bond of the monocationic molecule.

The pKa for the n'-amino function of nicotine is 8.4, calculated from after $^1$H-NMR. Therefore, a physiological pH, nicotine exists predominantly (>95%) in the monocationic n'-protonated species. However, in the case of the three quaternary ammonium compounds described in Table 5, the pKa of the N'-amino group is two units lower than in nicotine. This reduction in basicity of the pyrrolidino-N in the antagonist molecules is due to the existing positive charge on the molecule and also due to the β-electron withdrawing effect of the pyridinium moiety on the pyrrolidino N-atom. These two factors would make it more difficult to protonate the N'-amino group. Thus, at physiological pH, the antagonist molecules will exist predominantly in their unprotonated forms.

Figure 4:
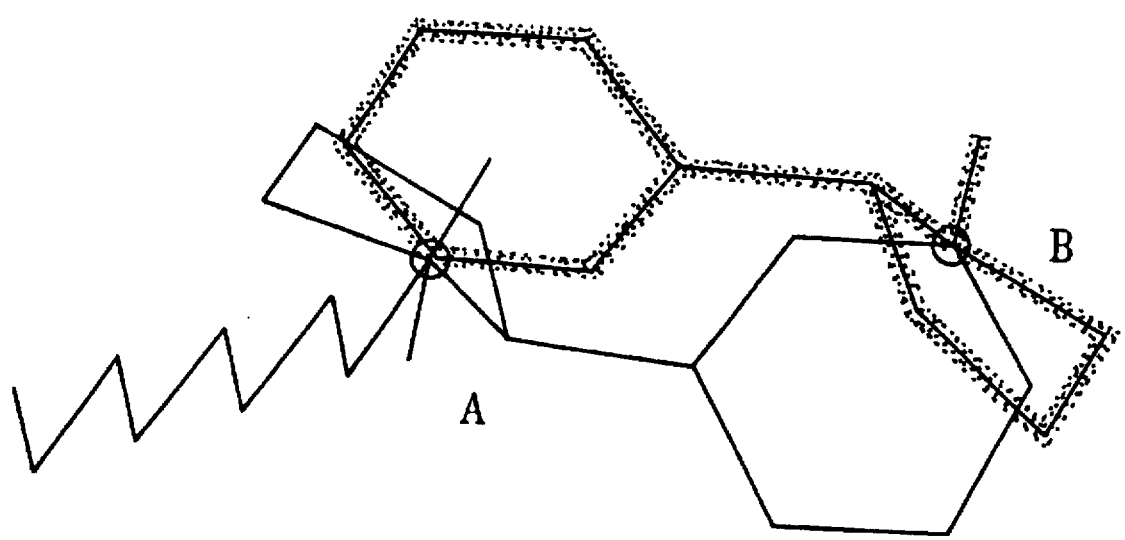
FIG. 4 shows overlay of the minimum energy conformers of protonated S(−)nicotine (red) and unprotonated S(−) NONI (black) showing the comparable N-N' intra-atomic distances in these molecules and the hypothetical mode of binding at the anionic site (A) and the hydrogen donor site (B) of the nicotinic receptor.

The nicotinic receptor pharmacophore incorporates a cationic center (i.e., a protonated pyrrolidine-N of S(−) nicotine) and an electronegative atom that is able to participate in a hydrogen-bond interaction with a receptor moiety (i.e., the pyridino-N of S(−)nicotine. From the present data, an antagonist binding mode for the quaternary ammonium nicotine analogues is suggested. The pyridinium-N atom in the antagonist molecules occupies the anionic site of the nicotine receptor that normally accommodates the protonated pyrrolidino-N functionality of the agonist S(−) nicotine. The unprotonated pyrrolidino-N atom of the antagonist then functions as the hydrogen-bond acceptor moiety. Thus, compared to the two nitrogen atoms in the nicotine molecule, the two nitrogen atoms in the antagonist molecules have interchanged their roles when binding to the nicotinic receptor, with a resulting change in activity from agonist to antagonist (FIG. 4). The size of the pyridino-N substituent is also an important factor governing antagonist efficacy. This appears to indicate the presence of an additional lipophilic binding site or pocket constituting another important component of the antagonist pharmacophore. This binding site extends beyond the normal agonist pharmacophore volume. Thus, interaction of the antagonist with this site may prevent the receptor protein from achieving the open channel quaternary form.

In sum, this work has resulted in the emergence of a new class of efficacious nicotinic antagonist which inhibit nicotine evoked [$^1$H]DA release from dopaminergic nerve terminals. These antagonists appear to interact with the nicotinic receptor modulating dopamine release in a novel binding mode and may serve as new tools for unraveling the complexities of neuronal nicotinic receptors.

For the purpose of this invention, the racemic mixtures and the dextro and levo forms are included within the present invention. The racemic mixtures and the dextro forms are preferred.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient.

Topical application can be in the form of ointments, creams, lotions, jellies, sprays, and the like. For oral administration either solid or fluid unit dosage forms can be prepared with the compounds of the invention. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the compounds of the invention can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral and suppository administration can also be obtained using techniques standard in the art. The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physiochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-Drug Delivery*, (Marcel Dekker, New York, N.Y. 1985); and Monkhouse et al, Transdermal drug deliver-problems and promises. *Drug Dev. Ind. Pharm.*, 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N<Ni-dimethylformamide, 1-dodecylazacycloheptan-2-one (Azone), propylene glycol, ethanol, pyrrolidones such as N-methyl-2-pyrrolidone (NMP) and surfactants. See Bronough et al, supra, and Stoughton et al, Azone: a New Non-toxic enhancer of percutaneous penetration. *Drug Dev. Inc. Pharm.*, 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans, Wells, D. A. et al: Disposition and Metabolism of Double-Labeled [$^3$H and $^{14}$C] N-methyl-2-pyrrolidone in the Rat. *Drug Met. Disps.*, 16, 243–249 (1988). Animal and human experiments have shown very little irritation or sensitization potential. Ames type assays and chronic exposure studies have not revealed any significant toxicity, Wells et al, Mutagenicity and Cytotoxicity of N-methyl-2-p[yrrolidone and 4-(methyl amino) Butanoic Acid in the Salmonella/microsome Assay. *J. Appl. Tox.*, 8, 135–139 (1988). N-methylpyrrolidone has also been shown to be an effective penetration enhancer. Barry et al, Optimization and Bioavailability of Topical Steroids: Penetration Enhancers Under Occlusion. *J. Inv. Derm.*, 82, 49–52 (1984); Akter et al, Absorption Through human Skin of Ibuprofen and Flurbiprofen; Effect of Dose Variation, Deposited Drug Films, Occlusion and the Penetration Enhancer N-methyl-2-pyrrolidone. *J. Pharm. Pharmacol.*, 37, 27–37 (1984); Holegaard et al, Vesical Effect on Topical Drug Delivery IV. Effect of N-methylpyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Non-occluded penetration Enhancers Under Thermodynamic Control. *J. Pharm. Pharmacol.*, 37, 298–304 (1985); Sasaki et al, Enhancing Effect of Pyrrolidone Derivatives on Transderman Drug Delivery. 1. *Ing. J. Pharm.*, 44, 14–24 (1988); lee et al, Toxicity of N-methyl-2-pyrrolidone (NMP): Tetratogenic, Subchronic and Two-year Inhalation Studies, *Fund. Appl., Tox.*, 9, 222–235 (1987).

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 10 to 400 mg when administered by either oral or rectal dose from 1 to 3 times daily. Preferably about 20 to about 200 mg are administered orally or rectally 1 to 3 times a day for an adult human. The required dose is considerably less when administered parenterally, preferably about 10 to about 50 mg may be administered intramuscularly or transdermally, 1 or 2 times a day for an adult human.

In sum the invention provides a compound of the following formula:

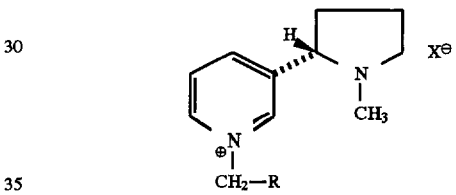

wherein R=N-alkyl or branched alkyl with 2–19 carbon atoms, cycloalkyl, aralkyl, N-alkenyl or alkenyl with 2–19 carbon atoms, and N-alkynyl or branched alkynyl with 2–19 carbon atoms; and X=Cl$^-$, Br$^-$, I$^-$, HSO$_4^-$, ½SO$_4^{2-}$. Compounds in which R is branched alkyl with 2–19 carbon atoms or R is a cycloalkyl or aralkyl group are preferred. In addition compounds wherein in X is I$^-$, are also preferred.

More particularly compounds selected from the group consisting of S-N-hydroxyethyl nicotinium iodide (NHENI), S-N-nbutyl nicotinium iodine (NnBNI), S-N-propyl nicotinium iodide (NPNI), S-N-benzyl nicotinium bromide (NBNB), S-N-octylnicotinium iodide (NONI), and S-N-allylnicotinium iodide (NANI) have been shown to have preferred nicotinic receptor antagonist activity.

The compounds of the invention can be used in a method of antagonizing the nicotinic receptor comprising administering a pharmaceutically effective amount of the compound.

DETAILED DESCRIPTION OF THE DRAWINGS

FIG. 1. Structures of S(−)nicotine and related compounds studied in [$^3$H]DA release assays. Abbreviated nomenclature is given in parentheses.

FIG. 2. IC50 values for N-substituted analogues of nicotine, nornicotine, and cotinine to inhibit nicotine-evoked [$^3$H]DA release from rat striatal slices. Inhibition produced by the classical nicotinic inhibitors, mecamylamine (MEC) and DHBE was also determined. Slices were superfused with inhibitor for 60 min following co-superfusion with 10 µM nicotine. Inhibition was determined by comparing [$^3$H]DA release in the absence and presence of various concentrations of inhibitor. IC50 values were determined using the Logit-log plot (pseudo-Hill plot). The analogue-induced percentage of inhibition (P) of [$^3$H]DA release evoked by S(−)nicotine (10 μM) was used to calculate log (P/[1-P]), which was plotted against the log concentration of analog. IC50 for each animal was determined as the intercept of the linear regression. For each analogue, the IC50 was obtained from the mean of the group of animals used for that analogue. Structures of the N-substituted compounds are given in FIG. 1.

FIG. 3. Space filling models of minimum energy conformers of N'-protonated S(−)nicotine and the unprotonated and protonated forms of NONI.

FIG. 4. Overlay of the minimum energy conformers of protonated S(−)nicotine (red) and unprotonated S(−)NONI (black) showing the comparable N-N intra-atomic distances in these molecules and the hypothetical mode of binding at the anionic site (A) and the hydrogen donor site (B) of the nicotinic receptor.

REFERENCES

Alkondon M. and Albuquerque E. X. (1991): Initial characterization of the nicotinic acetylcholine receptors in rat hippocampal neurons. J. Recept. Res. 11:1001–1021.

Barlow R. B. and Johnson O. (1989): Relations between structure and nicotine-like activity: X-ray crystal structure analysis of (−)cytisine and (−)lobeline hydrochloride and a comparison with (−)nicotine and other nicotine-like compounds. Br. J. Pharmacol. 98:799–808.

Barlow R. B., Johnson O., Howard J. A. K., Walton D. C. and Koellner G. (1989): A comparison of the crystal structure of some quaternary trimethylammonium salts related to dopamine and noradrenaline with those of the corresponding amines: A comment on their nicotine-like biological activities. Acta Cryst. B45:396–404.

Beers W. H. and Reich E. (1970): Structure and activity of acetylcholine. Nature 228:917–922.

Copeland J. R., Adem A. Jacob P. and Nordberg A. A. (1991): A comparison of the binding of nicotine and nornicotine stereoisomers to nicotinic binding sites in rat brain cortex. Naunyn Schmeidebergs Arch. Pharmacol. 343:123–127.

Deneris E. S., Connolly J., Rogers S. W. and Duvoisin R. (1991): Pharmacological and functional diversity of neuronal nicotinic acetylcholine receptors. Trends Pharmac. Sci. 12:34–40.

Dwoskin L. P. and Zahniser N. R. (1986): Robust modulation of [$^3$]dopamine release from rat striatal slices by D-2 dopamine receptors. J. Pharmacol. Exp. Ther. 239:442–453.

Dwoskin L. P., Buxton S. T., Jewell A. L. and Crocks P. A. (1993): S(−)-Nornicotine increases dopamine release in a calcium-dependent manner from superfused rat striatal slices. J. Neurochem. 60:2167–2174.

El-Bizri H. and Clarke P. B. S. (1994): Blockage of nicotinic receptor-mediated release of dopamine from striatal synaptosomes by chlorisondamine and other nicotinic antagonists administered in vitro. Br. J. Pharmacol. III:406–413.

Giorguieff-Chesselet M. F., Kemel M. L., Wandscheer D. and Glowinski J. (1979): Regulation of dopamine release by presynaptic nicotinic receptors in rat striatal slices: Effect of nicotine in a low concentration. Life Sci. 25:1257–1262.

Goldberg S. R., Risner M. E., Stolerman I. P., Reaville C. and Garcha H. S. (1989): Nicotine and some related compounds: Effects on schedule controlled behavior and discriminative properties in rats. Psychopharmacol. 97:285–302.

Grady S., Marks M. J., Wonnacott S. and Collins A. C. (1992): Characterization of nicotinic receptor-mediated [$^3$H]dopamine release from synaptosomes prepared from mouse striatum. J. Neurochem. 59:848–856.

Grenhoff J. and Svensson T. H. (1989): Pharmacology of nicotine. Br. J. Addict. 84:477–492, 1989.

Leutje C. W., Patrick J. and Séguéla P. (1990a): Nicotine receptors in the mammalian brain. FASEB J. 4:2753–2760.

Leutje C. W., Wada K., Rogers S., Abramson S. N., Tsuji K., Heinemann S. and Patrick J. (1990b): Neurotoxins distinguish between different neuronal nicotinic acetylcholine receptor subunit combinations. J. Neurochem. 55:632–640.

McKennis H. Jr, Turnbull L. B., and Bowman E. R. (1963): N-Methylation of nicotine and cotinine in vivo. J. Biochem. 238:719–723.

Mulle C., Vidal C., Benoit P. and Changeux J. P. (1991): Existence of different subtypes of nicotinic acetylcholine receptors in the rat habenulo-interpeduncular system. J. Neurosci. 11:2588–2597.

Pauling P. and Percher T. (1973): Neuromuscular blocking agents: structure and activity. J. Chem.-Biol. Interact. 6:351–365.

Petersen D. R., Norris K. J. and Thompson J. A. (1984): A comparative study of the disposition of nicotine and its metabolites in three inbred strains of mice. Drug Metab. Dispo. 12:725–731.

Pool W. F. (1987): R(+)-N-Methylnicotinium ion and nicotine metabolism. Ph.D. Thesis. University of Kentucky.

Rapier C., Lunt G. G. and Wonnacott S. (1988): Stereoselective nicotine-induced release of dopamine from striatal synapatosomes: Concentration dependence and repetitive stimulation. J. Neurochem. 50:1123–1130.

Rapier R., Lunt G. G. and Wonnacott S. (1990): Nicotinic modulation of [$^3$H]dopamine release from striatal synaptosomes: Pharmacological characterization. J. Neurochem. 54:937–945.

Rearill C., Jenner P., Kumar R. and Stolerman I. P. (1988): High affinity binding of [$^3$H](−)nicotine to rat brain membranes and its inhibition by analogues of nicotine. Neuropharmacol. 27:235–241.

Risner M. E., Goldberg S. R., Prada J. A. and Cone E. J. (1985): Effects of nicotine, cocaine and some of their metabolites on schedule controlled responding by beagle dogs and squirrel money. J. Pharmacol. Exp. Ther. 234:113–119.

Risner M. E., Cone E. J., Benowitz N. L. and Jacob P. J. (1988): Effects of stereoisomers of nicotine and nornicotine on schedule controlled responding and physiological parameters of dogs. J. Pharmacol. Exp. Ther. 244:807–813.

Role L. W. (1992): Diversity in primary structure and function of neuronal nicotinic acetylcholine receptor channels. Curr. Opin. Neurobio. 2:254–262.

Rowell P. R., Carr L. A. and Garner A. C. (1987): Stimulation of [$^3$H]dopamine release by nicotine in rat nucleus accumbens. J. Neurochem. 49:1449–1454.

Sargent P. B. (1993): The diversity of neuronal nicotinic acetylcholine receptors. Annu. Rev. Neurosci. 16:403–443.

Seeman J. I. and Whidby J. F. (1976): The iodomethylation of nicotine. An unusual example of competitive nitrogen alkylation. J. Org. Chem. 41:3824–3826.

Schulz D. W. and Zigmond R. E. (1989): Neuronal bungarotoxin blocks the nicotinic stimulation of dopamine release from rat striatum. Neurosci. Latt. 98:310–316.

Sheridan R. P., Ramaswamy N., Dixon J. S., Venkatarghavan R. (1986): The ensemble approach to distance geometry: Application to the nicotinic pharmacophore. J. Medicin. Chem. 29:899–906.

Shibagaki M., Matsushita H., Shibata S., Saito Y., Tsujiono Y. and Kaneko H. (1982): The selectivity in the N'-alkylation of nicotine. Heterocyclles 19:1641–1645.

Stalhandske T. (1970): Effects of increased liver metabolism of nicotine on its uptake, elimination and toxicity in mice. Acta Physiol. Scand. 80:222–234.

Vidal C. and Changeux J. P. (1989): Pharmacological profile of nicotinic acetylcholine receptors in rat pre-frontal cortex: An electrophysiological study in a slice preparation. Neuroscience 29:261–270. Wasserman N. H., Barrels E. and Erlanger B. F. (1979): Conformational properties of the acetylcholine receptor as revealed by studies with constrained depolarizing ligand. Proc. Natl. Acad. Sci. U.S.A. 76:256–259.

Westfall T. C., Grant H. and Perry H. (1983): Release of depamine and 5-hydroxytryptamine from rat striatal slices following activation of nicotinic cholinergic receptors. Gen Pharmac. 14:321–325.

Zumstein A., Karduck W. and Starke K. (1981): Pathways of depamine metabolism in rabbit caudate nucleus in vitro. Naunyn-Schmiedeberg's Arch. Pharmacol. 316:205–217.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A compound of the following formula:

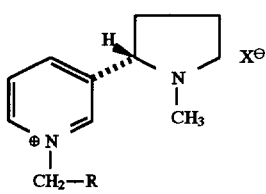

wherein R=branched alkyl with 4–19 carbon atoms, cycloalkyl, N-alkenyl or alkenyl with 4–19 carbon atoms, and N-alkynyl or branched alkynyl with 4–19 carbon atoms; and X=Cl$^-$, I$^-$, HSO$_4^-$, ½SO$_4^{2-}$.

2. A compound according to claim 1, wherein in R is branched alkyl with 4–19 carbon atoms.

3. A compound according to claim 1, wherein in X is I$^-$.

4. A compound according to claim 1, wherein said compound is selected from the group consisting of S-N-hydroxyethyl nicotinium iodide (NHENI), S-N-propyl nicotinium iodide (NPNI), S-N-benzyl nicotinium bromide (NBNB), S-N-octylnicotinium iodide (NONI), and S-N-allyl-nicotinium iodide (NANI).

5. A compound according to claim 4, wherein said compound has an order of potency wherein NONI>>MEC>>NPNI=NANI>NHENI>>>(±)di-N-allyl nicotinium iodide (DNANI)=(±)N-methyl nornicotinium iodide (NMNNI)=NMNI= S-N-methyl cotininium iodide (NMCI)=S-N'-methyl nicotinium iodide PIPNMN).

6. A compound according to claim 1, wherein said compound is a nicotinic receptor antagonist.

7. A compound according to claim 1, wherein said compound inhibits nicotine-evoked dopamine release.

8. A method of antagonizing the nicotinic receptor comprising administering a pharmaceutically effective amount of a compound according to the following formula:

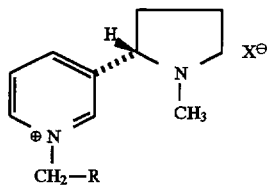

wherein R=N-alkyl or branched alkyl with 2–19 carbon atoms, cycloalkyl, aralkyl, N-alkenyl or alkenyl with 2–19 carbon atoms, and N-alkynyl or branched alkynyl with 2–19 carbon atoms; and X=Cl$^-$, Br$^-$, I$^-$, HSO$_4^-$, ½SO$_4^{2-}$ to a host in need of said treatment.

9. A method of treatment of a condition selected from the group consisting of abuse of nicotinic agonist drugs, smoking addiction, and nicotine intoxication comprising administering a pharmaceutically effective amount of a compound according to the following formula:

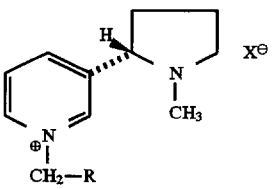

wherein R=N-alkyl or branched alkyl with 2–19 carbon atoms, cycloalkyl, aralkyl, N-alkenyl or alkenyl with 2–19 carbon atoms, and N-alkynyl or branched alkynyl with 2–19 carbon atoms; and X=Cl$^-$, Br$^-$, I$^-$, HSO$_4^-$, ½SO$_4^{2-}$ to a host in need of said treatment.

10. A method of treatment of Alzheimer's disease comprising administering a pharmaceutically effective amount of a compound of the following formula:

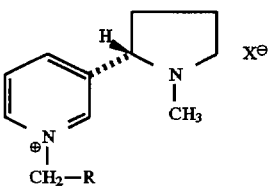

wherein R=N-alkyl or branched alkyl with 2–19 carbon atoms, cycloalkyl, aralkyl, N-alkenyl or alkenyl with 2–19 carbon atoms, and N-alkynyl or branched alkynyl with 2–19 carbon atoms; and X=Cl$^-$, Br$^-$, I$^-$, HSO$_4^-$, ½SO$_4^{2-}$ to a host in need of said treatment.

11. A compound according to claim 1 wherein said compound competitively inhibits central nervous system acting nicotinic agonists.

12. A compound according to claim 11 wherein said compound acts at the α3β2 neuronal nicotinic receptor in the central nervous system.

13. A method of treatment of Parkinson='s disease comprising administering a pharmaceutically effective amount of a compound according to the following formula:

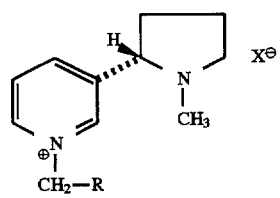
wherein R=N-alkyl or branched alkyl with 2–19 carbon atoms, cycloalkyl, aralkyl, N-alkenyl or alkenyl with 2–19 4–19 carbon atoms, and N-alkynyl or branched alkynyl with 2–19 carbon atoms; and X=Cl$^-$, Br$^-$, I$^-$, HSO$_4^-$, ½SO$_4^{2-}$ to a host in need of said treatment.
* * * * *